United States Patent [19]

Aritomi

[11] Patent Number: 4,958,637

[45] Date of Patent: Sep. 25, 1990

[54] MR EXAMINING APPARATUS OF HEART BEAT SYNCHRONOUS TYPE

[75] Inventor: Toshiaki Aritomi, Katsuta, Japan

[73] Assignee: Hitachi, Ltd., Tokyo, Japan

[21] Appl. No.: 278,843

[22] Filed: Dec. 2, 1988

[30] Foreign Application Priority Data

Dec. 4, 1987 [JP] Japan .................. 62-307030

[51] Int. Cl.$^5$ .............................................. A61B 5/05
[52] U.S. Cl. ................................ 128/653 A; 324/309; 324/322; 128/696
[58] Field of Search ................. 128/653, 696; 324/306, 324/309, 318, 322

[56] References Cited

U.S. PATENT DOCUMENTS

| | | | |
|---|---|---|---|
| 4,567,893 | 2/1986 | Charles et al. | 128/653 AF |
| 4,602,641 | 7/1986 | Feinberg | 128/653 AF |
| 4,709,212 | 11/1987 | MacFall et al. | 324/309 |
| 4,714,081 | 12/1987 | Dumoulin et al. | 128/653 AF |
| 4,716,368 | 12/1987 | Haake | 324/309 |
| 4,717,879 | 1/1988 | Riederer et al. | 324/309 |
| 4,727,882 | 3/1988 | Schneider et al. | 128/653 A |

*Primary Examiner*—Lyle L. Howell
*Assistant Examiner*—K. M. Pfaffle
*Attorney, Agent, or Firm*—Antonelli, Terry, Stout & Kraus

[57] ABSTRACT

A magnetic resonance examining apparatus of heart beat synchronous type in which one heart beat period is substantially equally divided to provide a plurality of phases, and at least some of those phases are selected as imaging phases so as to obtain nuclear magnetic resonance images. In the apparatus, spin excitation is effected at all the phases including those where nuclear magnetic resonance images are obtained and those where nuclear magnetic resonance images are not obtained, so that all the phases have the same longitudinal relaxation time after spin excitation. Therefore, nuclear magnetic resonance signals free from variations of the longitudinal relaxation time can be obtained to provide clear nuclear magnetic resonance images at anyone of the plurality of phases.

15 Claims, 5 Drawing Sheets

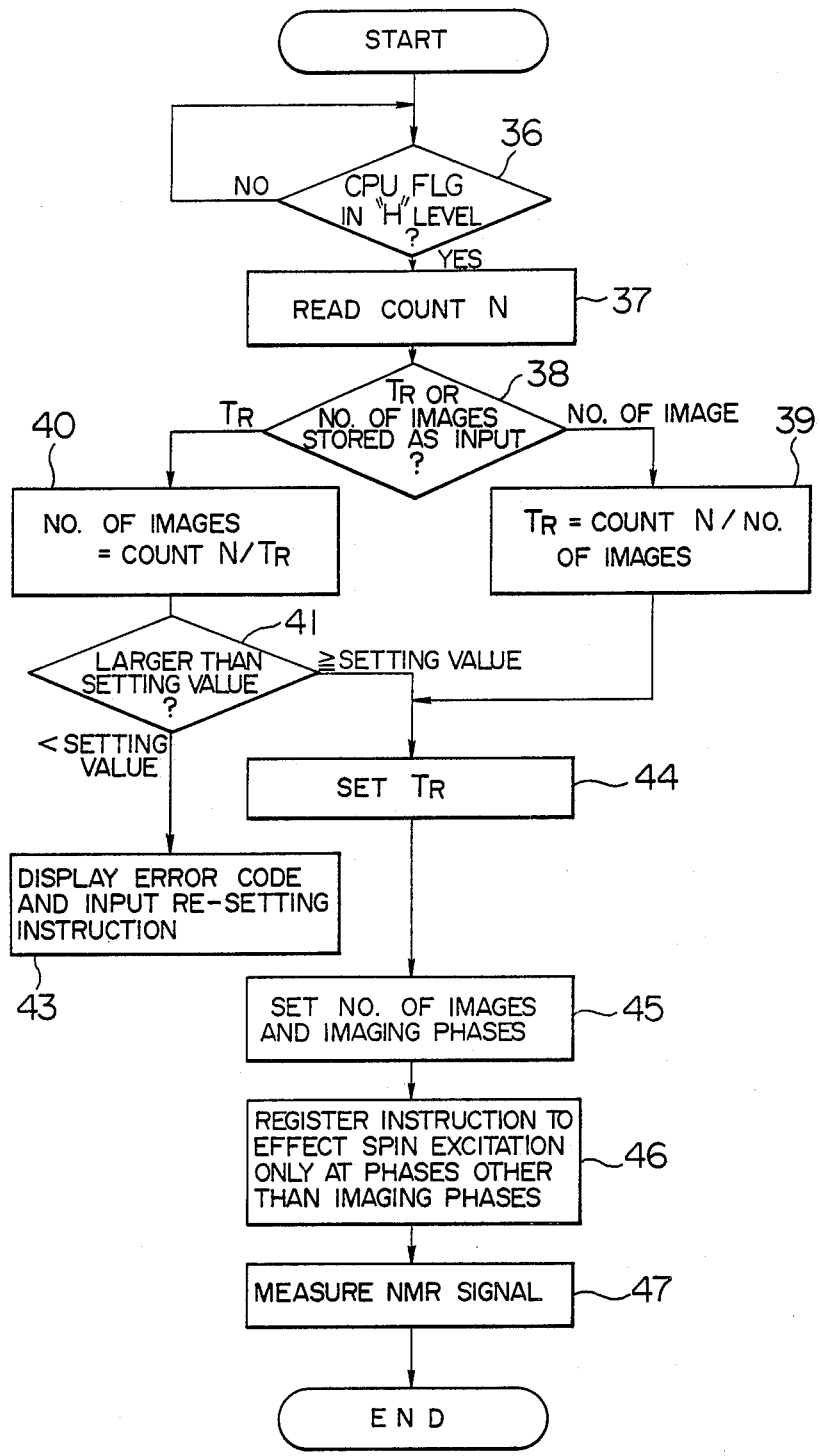

MR EXAMINING APPARATUS OF HEART BEAT SYNCHRONOUS TYPE

BACKGROUND OF THE INVENTION

This invention relates to a magnetic resonance examining apparatus of heart beat synchronous type, and more particularly to an apparatus of the kind described above in which a nuclear magnetic resonance signal (which will be referred to hereinafter as an NMR signal) is obtained in synchronism with a heart beat of a subject to be examined, and a nuclear magnetic resonance image (which will be referred to hereinafter as an NMR image) is formed on the basis of the NMR signal.

An NMR image is formed from an NMR signal obtained in each of a plurality of times of spin excitation in a subject being examined. A clear NMR image cannot be obtained because the position where an NMR signal is generated in each time of spin excitation differs depending on parts of the heart moving due to a heart beat. Therefore, it has been a common practice to obtain an NMR signal by effecting spin excitation in synchronism with a heart beat.

In the art of imaging by scanning in synchronism with a heart beat, an electrocardiograph is usually used as a synchronous detector. FIG. 1 shows a general heart beat waveform recorded on the electrocardiograph. In FIG. 1, the period of the P and Q waves corresponds to a period 17 of contraction of the atrium, the period of the QRST waves corresponds to a period 18 of contraction of the ventricle, and the period between the end of the T wave and the beginning of the P wave corresponds to an expansion period 19.

The R wave has a highest peak, and this peak is usually used as a trigger for starting a signal read sequence of examination.

However, according to such a manner of scan imaging, spin excitation is effected only once for each heart beat which takes a period of time of about 0.8 to 1.3 sec, and the resultant data is read or fetched. Therefore, a method called a multiphase imaging method well known in the art from the disclosure of, for example, "Journal of NMR Medicine", Vol. 6, September, 1986, Page 119 is now employed. According to this method, the R wave of a heart beat waveform is used as a trigger, and, after a predetermined time from this R wave, spin excitation is repeatedly effected a plurality of times at intervals of a predetermined repetition time A from the delay time as shown in FIG. 2 so as to obtain a plurality of NMR signals. Thus, an NMR image, that is, a phase image is obtained at each phase of spin excitation.

In the method of multiphase imaging described above, spin excitation is effected at the interval of the repetition time A at each phase where the NMR image is obtained. However, no spin excitation is effected at the phase where the NMR image need not be obtained. Therefore, the value of a repetition time B, in which no NMR image is obtained, differs from that of the spin-excitation repetition time A, and this means that the spin excitation is not continuously effected at a constant period. As a result, the state of recovery of longitudinal relaxation after the spin excitation at each phase is not uniform, and the NMR signals generated from the subject at individual phases will differ from each other, resulting in different contrasts of the NMR images obtained at individual phases.

SUMMARY OF THE INVENTION

It is an object of the present invention to provide a magnetic resonance (MR) examining apparatus of heart beat synchronous type which is used to obtain multiphase images in synchronism with the heart beat of a subject being examined and in which the state of recovery of longitudinal relaxation after spin excitation can be made uniform at individual phases so that clear NMR images having a good contrast can be formed.

According to the MR examining apparatus of heart beat synchronous type of the present invention, the length of time of one heart beat period is substantially equally divided, and spin excitation is effected at both of a phase where an NMR image is obtained and a phase where no NMR image is obtained thereby making uniform the state of recovery of the longitudinal relaxation after the spin excitation at individual phases, so that NMR signals having uniform conditions can be obtained when the NMR images at selected ones of all the phases are to be formed.

According to one aspect of the apparatus of the present invention, when the period of spin excitation is preselected, an integer closest to the value obtained by dividing one heart beat period by the period of spin excitation is found, and the heart beat period is divided by this integer to determine the period of spin excitation. Then, the number of phase images to be obtained and the number of imaging phases are determined, and NMR images are measured.

According to another aspect of the apparatus of the present invention, when the number of phase images is previously selected, one heart beat period is divided by the number of phase images to determine the period of spin excitation. Then, the number of phase images and the number of imaging phases are determined, and NMR images are measured.

BRIEF DESCRIPTION OF THE DRAWINGS

FIG. 6 is a flow chart of processing by the computer incorporated in the embodiment shown in FIG. 3.

DESCRIPTION OF THE PREFERRED EMBODIMENTS

A preferred embodiment of the apparatus according to the present invention will now be described in detail with reference to FIGS. 3 to 6.

Figure 1:
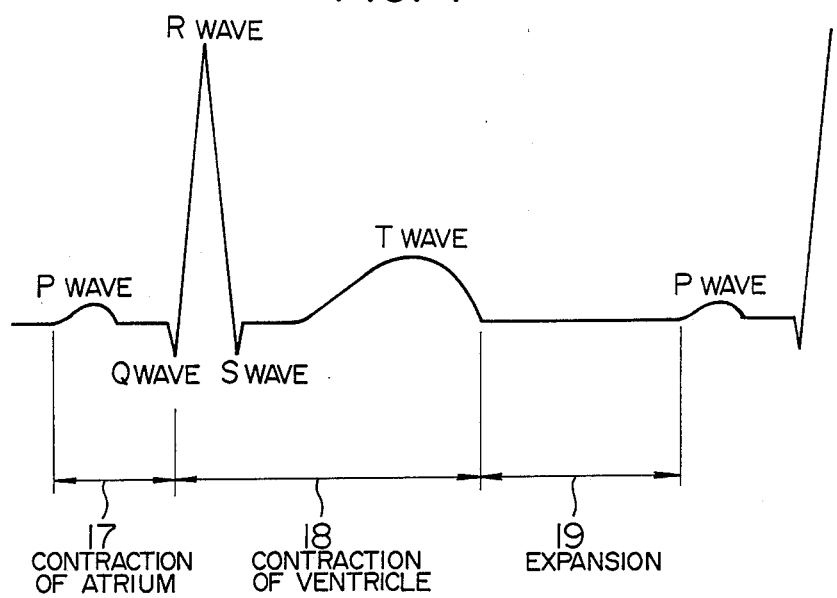
FIG. 1 shows a heart beat waveform recording on an electrocardiograph.
Figure 2:
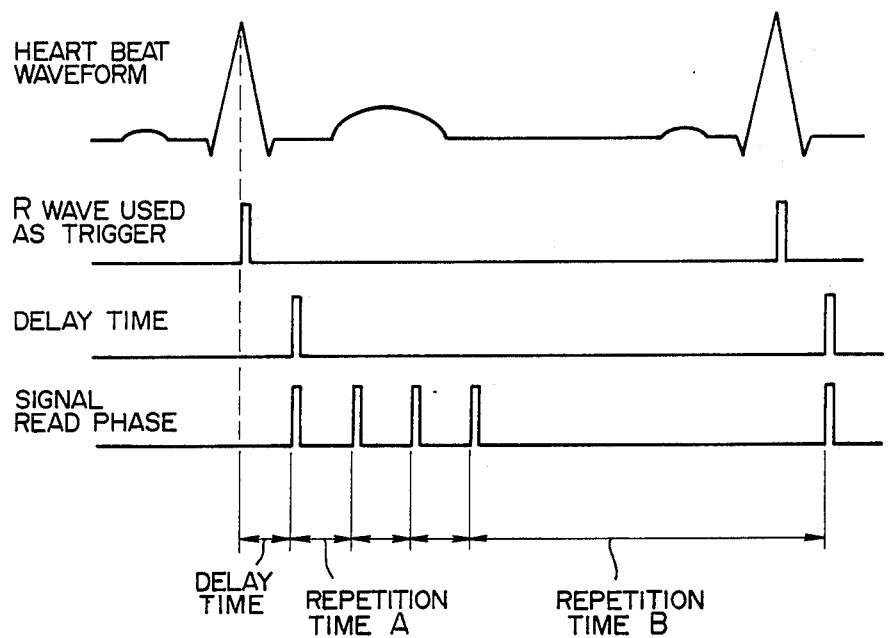
FIG. 2 shows waveforms illustrating a prior art sequence for reading or fetching NMR signals.
Figure 3:
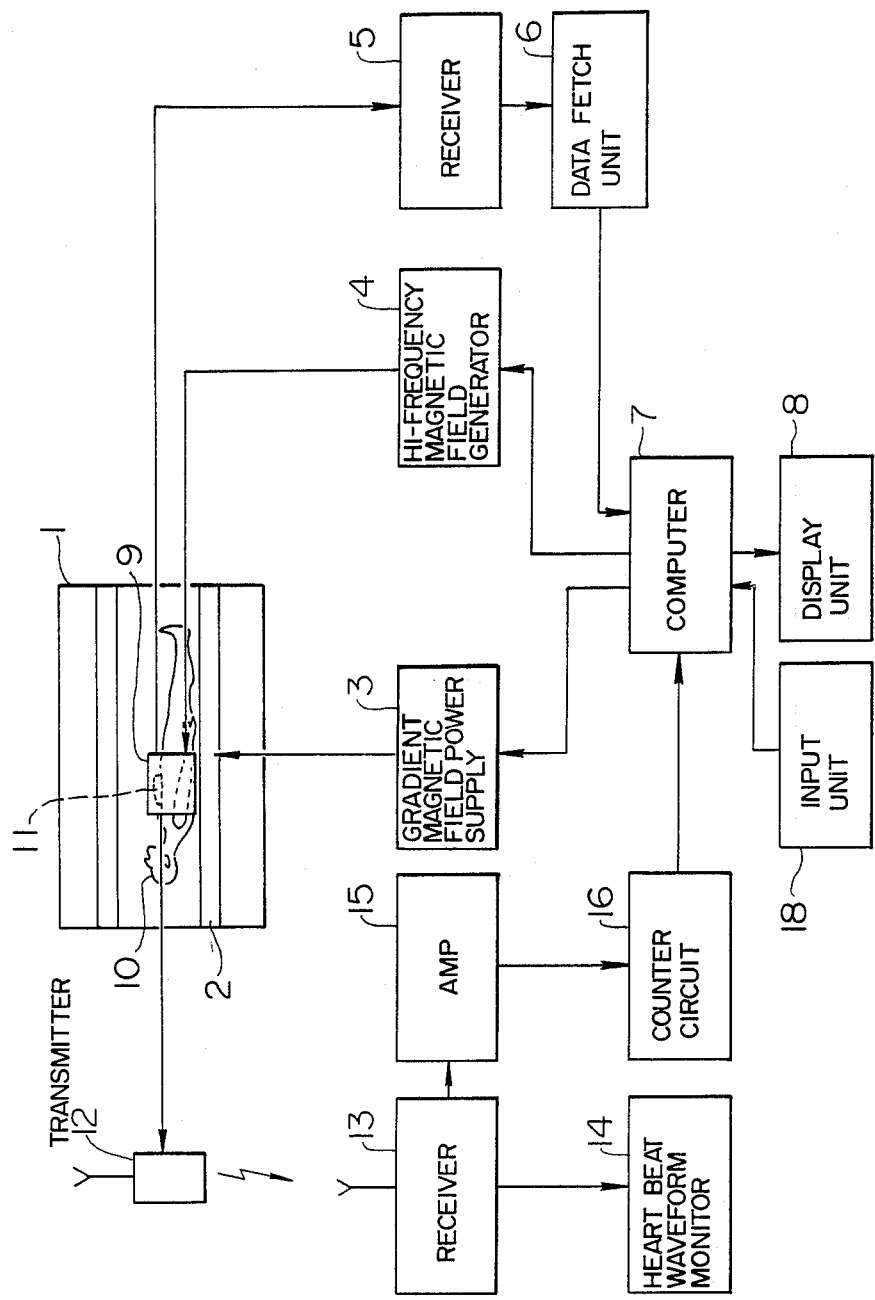
FIG. 3 is a block diagram showing the structure of an MR imaging system to which an embodiment of the present invention is applied.

FIG. 3 is a block diagram of an MR imaging system to which the apparatus according to the present invention is applied. Referring to FIG. 3, a superconducting magnet 1 generates a constant static magnetic field. An electrode 11 for sensing the heart action is mounted on the chest of the body of a subject 10 placed in the internal space of the superconducting magnet 1 and picks up an electrical signal representing the electromotive force generated from the heart muscle of the subject 10. This electrical signal will be referred to hereinafter as a heart beat signal. The heart beat signal is transmitted at a radio frequency from a transmitter 12 to a receiver 13 connected at its output to an amplifier 15 which amplifies the heart beat signal. The radio frequency used for transmission is about 150 MHz. The waveform of the heart beat signal received at the receiver 13 is displayed on a heart beat waveform monitor 14. The output signal of the amplifier 15 is applied to a counter circuit 16.

Figure 4:
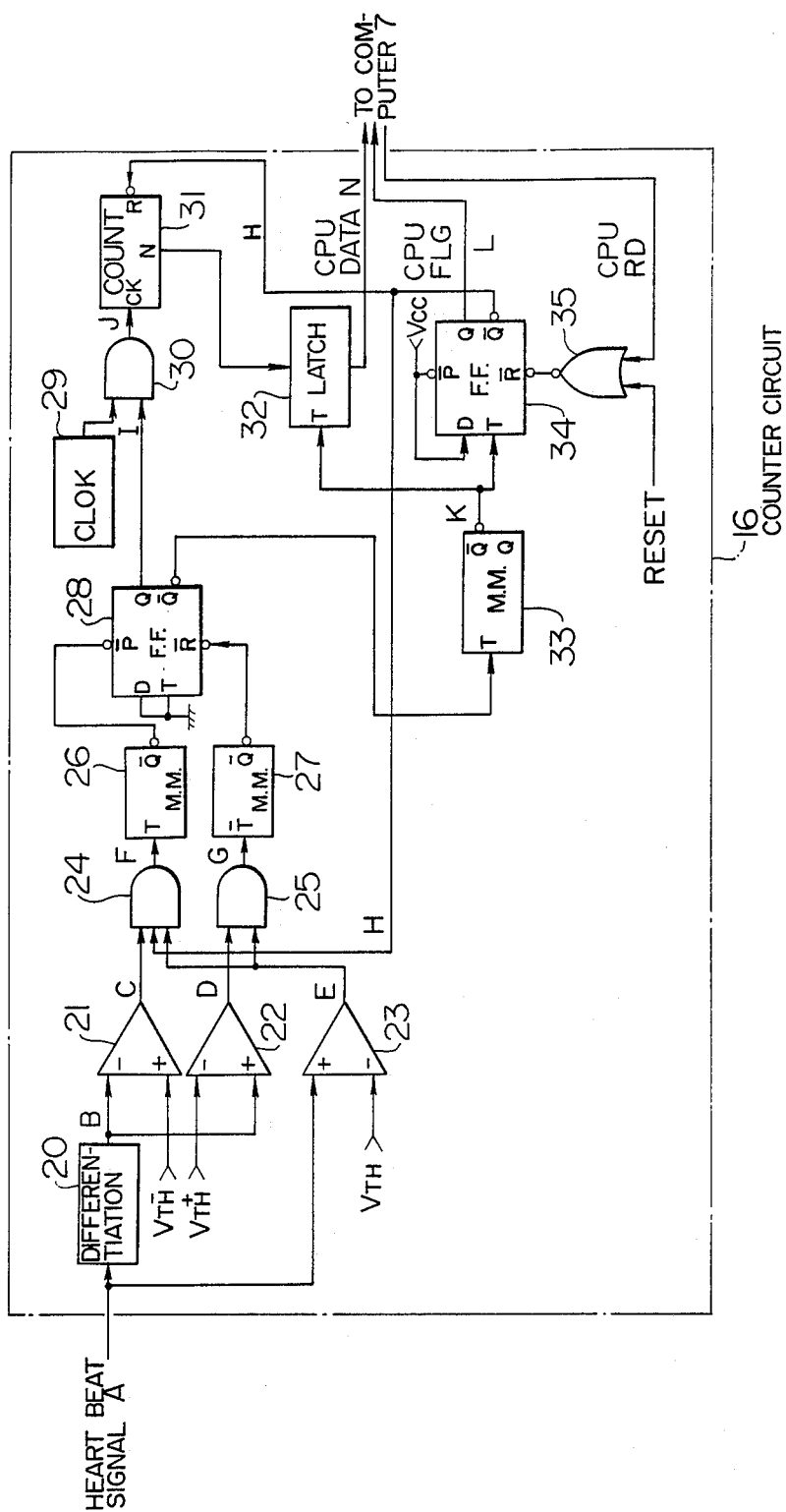
FIG. 4 is a block diagram showing the detailed structure of the counter circuit shown in FIG. 3.
Figure 5:
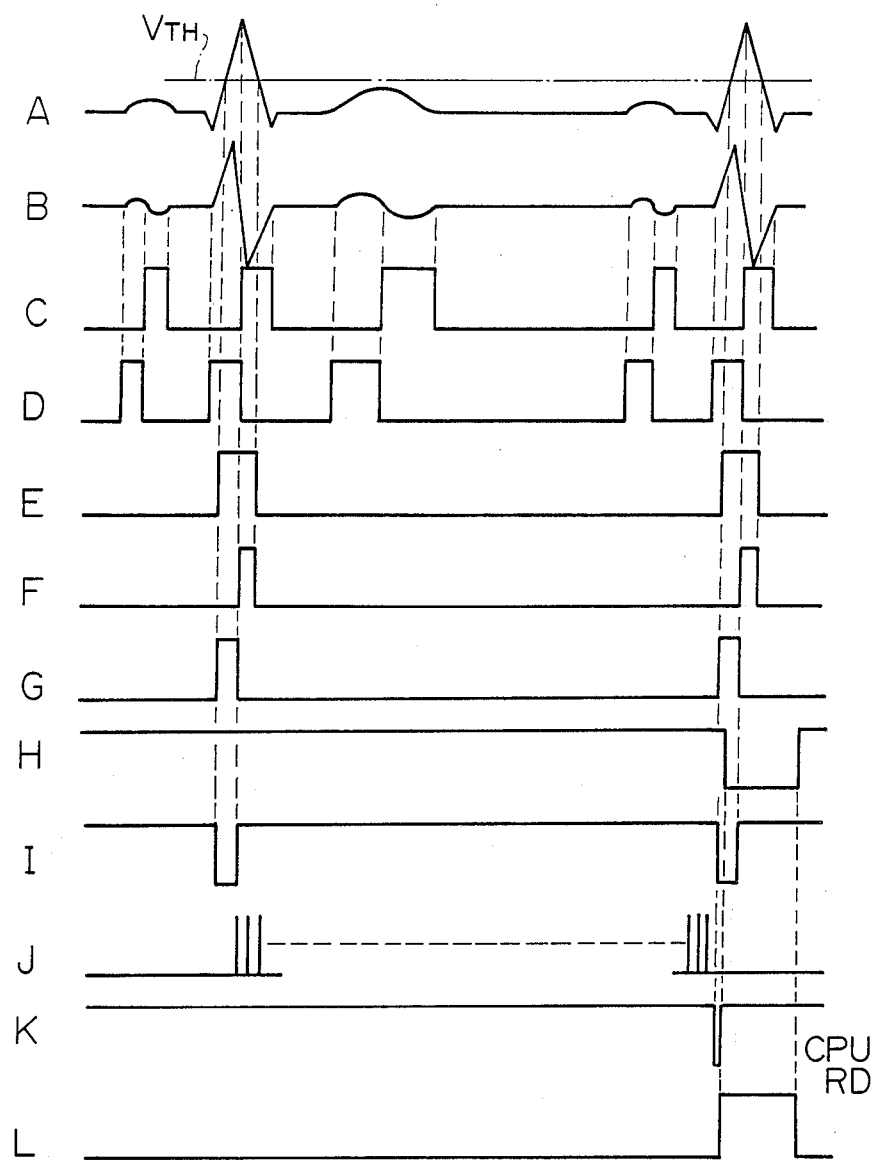
FIG. 5 is a timing chart of operation of the counter circuit shown in FIG. 3.

The operation of the counter circuit 16 will be described in detail with reference to FIGS. 4, 5 and 6. FIG. 4 is a block diagram showing the detailed structure of the counter circuit 16, FIG. 5 shows waveforms appearing at principle parts of the counter circuit 16, and FIG. 6 is a flow chart of processing by a computer 7 shown in FIG. 3. Waveforms of output signals of principal parts of the counter circuit 16 shown in FIG. 4 are designated by symbols A to L and shown in FIG. 5.

The heart beat signal A amplified by the amplifier 15 shown in FIG. 3 is differentiated by a differentiation circuit 20 shown in FIG. 4, and a differentiated signal B having a waveform as shown in FIG. 5 appears from the differentiation circuit 20. This differentiated waveform signal B is applied to analog comparators 21 and 22 to be compared with threshold levels $V_{TH}^-$ and $V_{TH}^+$ respectively. As a result, output signals C and D having waveforms as shown in FIG. 5 appear from the comparators 21 and 22 and represent the negative and positive waveform portions respectively of the output signal B of the differentiation circuit 20. The heart beat signal A is also applied to another comparator 23 to be compared with a threshold level $V_{TH}$, and an output signal E having a waveform as shown in FIG. 5 appears from the comparator 23.

The signals C and E are applied to an AND gate 24, while the signals D and E are applied to another AND gate 25, and output signals F and G having waveforms as shown in FIG. 5 are applied from the AND gates 24 and 25 to monostable multivibrators (MM's) 26 and 27 respectively. A flip-flop (FF) circuit 28 connected to the MM's 26 and 27 generates an output signal I which rises in response to the leading edge of the signal F and falls in response to the trailing edge of the signal G as shown in FIG. 5. The signal I is applied to an AND gate 30. This signal I has a pulse width corresponding to the period of time between an R wave and the next R wave in the heart beat signal A. Therefore, clock pulses generated from a clock generator 29 are permitted to pass through the AND gate 30 during a period of time which is substantially equal to the length of time of one period of the heart beat signal A. A counter 31 counts the number of clock pulses J passed through the AND gate 30, and, after the count N is latched in a latch circuit 32.

Suppose, for example, that the frequency of the clock signal generated from the clock generator 29 is 2 kHz. Then, when the time interval between the consecutive R waves is 1 sec, the number of clock pulses counted between the R waves is 2,000+1, provided that a measurement error of 0.5 msec occurs. As soon as the counting operation counting the number of clock pulses between the R waves is completed, an MM 33 is triggered by the trailing edge of the gate signal I applied from the FF circuit 28, and an output signal K having a waveform as shown in FIG. 5 appears from the MM 33. As soon as the count N of the counter 31 is latched in the latch circuit 32 in response to the application of the signal K, a flag signal L having a waveform as shown in FIG. 5 appears from an FF circuit 34 to be applied to the computer 7. When this flag signal L is detected, the computer 7 reads the count N latched in the latch circuit 32. After the computer 7 reads the count N, the computer 7 applies a reset signal $R_D$ to the FF circuit 34 through a NOR gate 35, with the result that the FF circuit 34 generating the flag signal L is now reset. The other input terminal of the NOR gate 35 is used to reset the FF circuit 34 by a reset signal generated when the system power supply is turned on. The FF circuit 34 generates an output pulse signal H having a waveform inverted relative to that of the signal L as shown in FIG. 5. Therefore, when the computer 7 cannot read the count N latched in the latch circuit 32 until the next heart beat period is started, the signal H acts to prevent the counter 31 from starting to count the clock pulses, so that an incomplete NMR signal may not be measured.

The operation of the computer 7 will now be described with reference to the flow chart of FIG. 6. As soon as the flow is started, decision is made in a step 36 as to whether or not the flag signal L generated from the FF circuit 34 is in its "H" level. When the result of decision in the step 36 proves that the flag signal L is in its "H" level, the count N latched in the latch circuit 32 is read out in a step 37. When the computer 7 reads the count N, decision dicision is made in a step 38 as to whether data of a repetition time $T_R$ or the number of required phase images is previously set as an input in an input unit 18 shown in FIG. 3. The term "repetition time $T_R$" is used herein to indicate the case where the operator of the computer 7 previously sets the period $T_R$ of spin excitation. Also, the term "number of required phase images" is used herein to indicate the case where the operator of the computer 7 previously sets the number of phase images required for imaging. When the result of decision in the step 38 proves that the repetition time $T_R$ is the input previously set by the operator, the count N is divided by the repetition time $T_R$ in a step 40 to compute the number of phase images that can be imaged, and, in a step 41, decision is made as to whether or not the computed number of phase images is larger than the previously-set number (the setting) of phase images to be imaged. When the result of decision in the step 41 proves that the setting is larger than the computed value, an error code and an input re-setting instruction are displayed in a step 43 on a display unit 8. On the other hand, when the setting of the number of phase images is smaller than or equal to the computed value, the repetition time $T_4$ is corrected in a step 44 until the number of phase images computed in the step 40 becomes an integer. That is, the value obtained by the computation in the step 40 is rounded to the nearest integer, and the count N is now divided by the imager to use the result of division as the timing or period of spin excitation.

Then, in a step 45, the number of phase images previously selected as the input is set together with the number of phases required for imaging, and, in a step 46, an instruction is registered which instructs that spin excitation only is to be effected at phases other than the predetermined imaging phases, and no data are to be acquired at such phases. Then, in a step 47, a predetermined sequence of NMR measurement is executed to measure NMR signals.

On the other hand, when the result of decision in the step 38 proves that the number of required phase images is the input previously set in the input unit 18, the count N is divided by the number of required phase images in a step 39 so as to determine the repetition time $T_R$. Subsequently, the steps 44 to 47 are similarly executed to complete the measurement of NMR signals.

The sequence of NMR measurement will now be described.

After the aforementioned conditions are set in the steps 44 to 46, a high-frequency magnetic field generator 4, a gradient magnetic field power supply 3 and a gradient magnetic field coil 2 are controlled by the computer 7 in synchronism with the trigger signal G and according to a data read or fetch sequence well known in the art. As a result, a high-frequency receiver coil 9 effects spin excitation at the desired tomographic section of the heart of the subject 10. An echo signal generated due to the spin excitation is received by a receiver 5 and supplied to a data read or fetch unit 6 under control of the computer 7. For each of individual echo signals supplied to the data fetch part 6, a suitable number of integrations and Fourier transformations are carried out for reconstructing the image. The reconstructed image is displayed on the display unit 8.

A method called a Cine-imaging method is now being increasingly employed in this field of art. According to this method, ten to twenty images at different phases between the R waves of one heart beat waveform are taken utilizing the method of high-speed imaging under the condition that the repetition time $T_4$ is $T_4 < T_1$, where $T_1$ is the longitudinal relaxation time, and such images are continuously cinematically displayed to display the motion of the heart of a subject. When this cine-imaging method is utilized with the imaging apparatus according to the present invention, the combination can exhibit an especially marked effect.

According to the present invention, a trigger signal is divided in synchronism with the R wave of the heart beat waveform and applied to open a gate during the length of time of one heart beat between the R wave and the next R wave. A counter counts the number of pulses spaced by a constant time interval, that is, the number of reference clock pulses permitted to pass through the gate during the above length of time. On the basis of the count of the counter and the repetition time of spin excitation or the number of phase images previously supplied as an input, a computer computes the optimum repetition time of spin excitation and the optimum number of phase images while taking into account the longitudinal relaxation time required after the spin excitation, so as to excite the spin and obtain resultant NMR signals. Therefore, clear multiphase images of the heart having a good contrast can be obtained

I claim:

1. A magnetic resonance examining apparatus of heart beat synchronous type for imaging multiphase images in synchronism with a heart beat of a subject, said apparatus comprising:
    means for detecting a heart beat waveform of the subject;
    means for generating a synchronizing signal synchronous with the heart beat waveform detected by said detecting means;
    means for measuring a repetition period of said heart beat waveform on the basis of the synchronizing signal applied from said synchronizing signal generating means;
    input means for inputting a previously stored setting of a repetition time for spin excitation of the subject;
    means responsive to said measuring means and said input means for computing a corrected repetition time close to said spin excitation repetition time on the basis of data of said heart beam waveform repetition period supplied from said measuring means and the setting of said spin excitation repetition time supplied from said input means, said corrected repetition time having a value which, when multiplied by a factor of N (N: an integer), becomes equal to that of said heart beat waveform repetition period;
    means for setting a plurality of imaging phases so as to form nuclear magnetic resonance images; and
    means for effecting spin excitation of the subject according to the corrected repetition period;
    means for setting a plurality of imaging phases so as to form nuclear magnetic resonance images; and
    means for effecting spin excitation of the subject according to the corrected repetition time computed by said corrected repetition time computing means and acquiring a nuclear magnetic resonance signal for each of the imaging phases set by said imaging phase setting means.

2. An MR examining apparatus according to claim 1, wherein said synchronizing signal generating means generates said synchronizing signal in synchronism with an R wave of said heart beat waveform.

3. An MR examining apparatus according to claim 1, wherein said measuring means includes clock pulse generating means, and counter means measuring said heart beat waveform repetition period by counting the number of clock pulses generated from said clock pulses generating means during a period of time substantially equal to one period of said heart beat waveform.

4. An MR examining apparatus according to claim 1, wherein said corrected repetition time computing means includes means for dividing the value of said heart beat waveform repetition period supplied from said measuring means by a value of said spin excitation repetition time supplied from said input means, and means for correcting said spin excitation repetition time until a result of computation by said dividing means becomes substantially equal to an integer.

5. An MR examining apparatus according to claim 4, wherein said correcting means includes means for determining said corrected repetition time in accordance with a rounding of the result of computation by said dividing means to said integer.

6. An MR examining apparatus according to claim 1, wherein said imaging phase setting means further includes means for setting a number of said imaging phases.

7. An MR examining apparatus according to claim 1, wherein said imaging phase setting means further includes means for registering an instruction which instructs that spin excitation only is to be effected at phases other than the imaging phases.

8. An MR examining apparatus according to claim 1, wherein said imaging phase setting means includes means for instructing that the imaging is to be effected at all the phases.

9. An MR examining apparatus according to claim 1, wherein said imaging phase setting means includes means for instructing that the imaging is to be effected at freely selected ones among all the phases.

10. An MR examining apparatus according to claim 1, further comprising:

means for applying a constant static magnetic field to the subject;

means for applying a gradient magnetic field to the subject;

means for applying a high-frequency magnetic field to the subject;

means for controlling said gradient and high-frequency magnetic field applying means;

means for receiving a NMR signal from the subject;

means for reconstructing an image on the basis of said received NMR signal; and means for displaying said reconstructed image.

11. A magnetic resonance examining apparatus of heart beat synchronous type for imaging multiphase images in synchronism with a heart beat of a subject, said apparatus comprising:

means for detecting a heart beat waveform of the subject;

means for generating a synchronizing signal synchronous with the heart beat waveform detected by said detecting means;

means for measuring a repetition period of said heart beat waveform on the basis of the synchronizing signal applied from said synchronizing signal generating means;

input means for inputting a previously stored setting of a repetition time for spin excitation of the subject and a previously stored setting of the number of phase images;

means responsive to said measuring means and said input means for computing a number of phase images that can be imaged on the basis of data of said heart beat repetition period supplied from said measuring means and the setting of said spin excitation repetition time supplied from said input means;

means for computing a corrected repetition time close to said spin excitation repetition time on the basis of the computed number of phase images computed by said phase image number computing means and the setting of said spin excitation repetition time supplied from said input means;

means for comparing the computed number of phase images computed by said phase image number computing means with the setting of the number of phase images supplied from said input means so as to confirm whether or not the computed number of phase images is equal to or larger than the setting of the number of phase images supplied from said input means; and means for effecting spin excitation of the subject according to the corrected repetition time computed by said corrected repetition time computing means and acquiring a nuclear magnetic resonance signal for each of the imaging phases stored in said input means, only when said comparing means confirms that the computed number of phase images is equal to or larger than the set number of phase images set in said input means.

12. An MR examining apparatus according to claim 11, wherein said comparing means further includes means for displaying an error code when the computed number of phase images is smaller than the setting of the number of phase images set in said input means.

13. An MR examining apparatus according to claim 11 further comprising:

means for applying a constant static magnetic field to the subject;

means for applying a gradient magnetic field to the subject;

means for applying a high-frequency magnetic field to the subject;

means for controlling said gradient and high-frequency magnetic field applying means;

means for receiving an NMR signal from the subject;

means for reconstructing an image on the basis of said received NMR signal; and means for displaying said reconstructed image.

14. A magnetic resonance examining apparatus of heart beat synchronous type for imaging multiphase image in synchronism with a heart beat of a subject, said apparatus comprising:

means for detecting a heart beam waveform of the subject;

means for generating a synchronizing signal synchronous with the heart beat waveform detected by said detecting means;

means for measuring a repetition period of said heart beat waveform on the basis of the synchronizing signal applied from said synchronizing signal generating means;

input means for inputting a previously stored setting of the number of phase images to be imaged;

means responsive to said measuring means and said input means for computing a repetition time for spin excitation of the subject on the basis of data of said heart beat waveform repetition period supplied from said measuring means and the setting of the number of phase images supplied from said input means;

means for setting a plurality of imaging phases so as to form nuclear magnetic resonance images; and means for effecting spin excitation of the subject according to the repetition time computed by said spin excitation repetition time computing means and acquiring a nuclear magnetic resonance signal for each of the imaging phases set by said imaging phase setting means.

15. An MR examining apparatus according to claim 12, further comprising:

means for applying a constant static magnetic field to the subject;

means for applying a gradient magnetic field to the subject;

means for applying a high-frequency magnetic field to the subject;

means for controlling said gradient and high-frequency magnetic field applying means;

means for receiving an NMR signal from the subject;

means for reconstructing an image on the basis of said received NMR signal; and means for displaying said reconstructed image.

* * * * *